United States Patent [19]

Bernard

[11] Patent Number: 5,183,459
[45] Date of Patent: Feb. 2, 1993

[54] EMULSION PRESSURE-SENSITIVE ADHESIVE POLYMERS IN BANDAGE AND MEDICAL TAPE CONSTRUCTIONS

[75] Inventor: Margaret M. Bernard, La Verne, Calif.

[73] Assignee: Avery Dennison Corporation, Pasadena, Calif.

[21] Appl. No.: 847,957

[22] Filed: Mar. 5, 1992

Related U.S. Application Data

[63] Continuation-in-part of Ser. No. 567,141, Aug. 14, 1990, which is a continuation-in-part of Ser. No. 393,970, Aug. 14, 1989, abandoned.

[51] Int. Cl.$^5$ ............................................. A61F 13/00
[52] U.S. Cl. .......................................... 602/52; 602/54
[58] Field of Search ..................................... 602/52, 54

[56] References Cited

U.S. PATENT DOCUMENTS

| | | | |
|---|---|---|---|
| 4,212,785 | 7/1980 | Turck | 526/317 |
| 4,354,008 | 10/1982 | Skoultchi | 525/370 |
| 4,564,664 | 1/1986 | Chang et al. | 526/325 |
| 4,759,983 | 7/1988 | Knutson et al. | 526/316 |
| 4,908,403 | 3/1990 | Spada et al. | 526/316 |
| 4,987,186 | 1/1991 | Akiyama et al. | 525/107 |

*Primary Examiner*—Joseph L. Schofer
*Assistant Examiner*—N. Sarofim
*Attorney, Agent, or Firm*—Christie, Parker & Hale

[57] ABSTRACT

Inherently tacky, emulsion pressure-sensitive adhesive polymers comprising about 35 to about 65 percent by weight alkyl acrylates, about 15 to about 35 percent vinyl esters, about 20 to about 35 percent by weight diesters of a dicarboxylic acid, and up to about 5 percent by weight of an unsaturated carboxylic acid formed in the presence of a reactive surfactant and having a gel content of about 50 to 70 percent by weight as formed are used in sterilizable bandage and medical tape constructions.

20 Claims, 1 Drawing Sheet

5,183,459

EMULSION PRESSURE-SENSITIVE ADHESIVE POLYMERS IN BANDAGE AND MEDICAL TAPE CONSTRUCTIONS

CROSS-REFERENCE TO RELATED APPLICATIONS

This is a Continuation-in-Part of application Ser. No. 07/567,141, filed Aug. 14, 1990 which is a Continuation-in-Part of application Ser. No. 07/393,970 filed Aug. 14, 1989, now abandoned, each incorporated herein by reference.

BACKGROUND OF THE INVENTION

The present invention relates to polymers which are inherently tacky and, as formed and sterilized are functional as pressure-sensitive adhesives in bandage and medical tape constructions. More particularly, the emulsion adhesives of the instant invention because of excellent room- and low-temperature performance and provide an ecologically safe replacement for adhesives and currently used in bandage and medical tape constructions which require aggressive adhesion to skin and resistance to moisture.

Self adhesive bandages and medical tapes have existed for a long time. Their constructions are similar but differ in that a bandage normally has a gauze bonded to the adhesive and is protected by a release liner. In addition, bandages come in a greater variety of shapes and sizes than tapes. The adhesives and backing materials for both may be the same. Both require the ability to be sterilized without material loss of adhesive properties and it is desirable for the adhesive to be hypoalergenic. This is not a characteristic of rubber based adhesives.

A medical tape is typically slit from a roll of a face stock or backing having on at least one surface thereof an adhesive which will adhere to skin under all conditions without irritation nor have an adhesion so great that the tape can be removed only with accompanying discomfort.

Bandages have the same requirement but differ from tapes in that they are die cut to select sizes, with the adhesive protected by a discardable release liner and a portion of the adhesive surface is bonded to a gauze which covers a wound. The traditionally used adhesives are rubber based solvent adhesives which are not hypoalergenic.

A need exists for pressure-sensitive acrylic adhesives of controlled properties which serve to supplant current used adhesives in bandage and medical tape constructions.

SUMMARY OF THE INVENTION

According to the present invention, there is provided a construction of a face stock or backing suitable for bandage and medical tape use having on at least one surface thereof an inherently tacky sterilizable acrylic emulsion adhesive polymers having excellent adhesion to skin under a variety of conditions. Moreover the acrylic polymers used in accordance with the invention are hypoalergenic.

The inherently tacky, emulsion pressure-sensitive adhesive polymers used in the bandage and tape constructions of the invention comprise on a polymerized basis and based on the total weight of the polymer, at least one alkyl acrylate containing from about 4 to about 8 carbon atoms in the alkyl group, preferably 2-ethylhexyl acrylate, said alkyl acrylate present in a total amount of from about 35 to about 60 percent by weight; at least one vinyl ester containing from 2 to about 16 carbon atoms in the alkyl chain of the acid, preferably vinyl acetate, said vinyl ester present in a total amount of from about 15 to about 35 percent by weight; at least one diester of a dicarboxylic acid wherein each alkyl group of the diester independently contains from about 6 to 12 carbon atoms, with di-2-ethylhexyl maleate or di-2-ethyl hexyl fumarate being preferred, said diesters being present in a total amount of from about 20 to about 40 percent by weight; up to about 5 percent by weight, preferably about to 3 percent, of an unsaturated carboxylic acid containing from 3 to about 5 carbon atoms, preferably acrylic and/or methacrylic acid. The emulsion polymer normally have a glass transition temperature of less than about −20° C. and a gel content as formed of from about 50 to about 70 percent by weight of the polymer. The emulsion adhesive polymers are formed using a reactive surfactant which polymerizes and becomes part of the emulsion polymer and which has been observed to enhance cohesive strength and aid in copolymerization of the monomers in forming the emulsion pressure-sensitive adhesive polymers of the instant invention. The amount of reactive surfactant employed in the preparation of the emulsion pressure-sensitive adhesives is in a positive amount up to about 0.4 percent by weight of the total monomers, preferably from about 0.1 to about 0.25 percent by weight. The preferred reactive surfactants are anionic vinyl functional surfactants, such as sodium vinyl sulfonate and sodium styrene sulfonate.

The emulsion adhesives may be prepared with excellent conversions at reaction temperatures ranging from 70° to about 85° C. in the presence of from about 0.5 to about 1 percent by weight, based on the weight of the monomers, of a persulfate or equivalent catalyst, with the monomer mix being fed over a period of about 4 to about 5 hours. Reaction pH is from about 2.5 to about 4.0. Conversion is high, approaching 100 percent at the reaction conditions set forth above.

The polymers may be sterilized by exposure to ethylene oxide, actinic radiation including gamma radiation, and electron beam radiation. With sterilization by actinic or electron beam radiation a significant improvement in cohesive strength can be achieved without significant loss of peel and tack.

In the construction of the bandages and medical tapes the emulsion adhesives of the invention may be directly coated onto the backing or coated onto a release surface and transferred to the backing.

THE DRAWINGS

FIG. 1 depicts typical bandage construction.
FIG. 2 depicts a typical medical tape construction.

DETAILED DESCRIPTION

The present invention relates to bandages and medical tapes constructions which employ acrylic emulsion pressure-sensitive adhesives which provide a desired level of aggressive adhesion to skin under moist conditions and with excellent cohesive strength. The adhesives have properties sufficient to make them useful for replacing solvent polymers including tackified elastomeric pressure-sensitive adhesives. The adhesive exhibits excellent aging and no edge ooze or bleed as part of bandage or tape laminate constructions. In addition, being functional as a single polymer, there is a minimal or no need for compounding and tackification. The improved performance characteristics of the adhesive of the instant invention enable them to be used on any available backing or face stock used in bandage and tape construction. Properties induced in the adhesive by proper selection of monomers and surfactants provide excellent moisture resistance.

Figure 1:
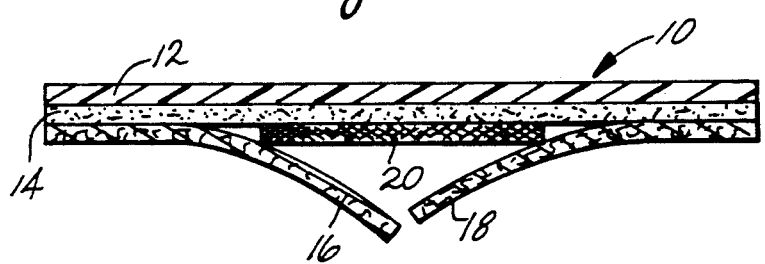
Figure 2:
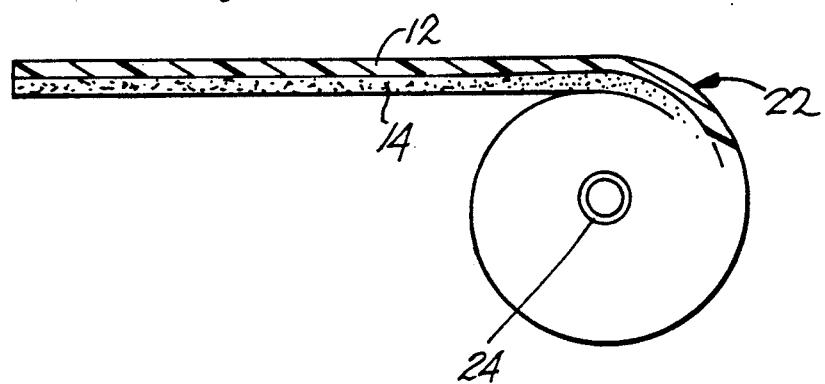

FIGS. 1 and 2 there is shown typical constructions for an adhesive bandage and medical tape.

With reference to FIG. an adhesive bandage 10 comprises a backing or face stock 12 having coated on one surface thereof a self adhesive or pressure-sensitive adhesive layer 14 which is protected by release liner segments 16 and 18 and supports gauze 20.

With reference to FIG. 2 a medical tape consists of backing 12 and adhesive 14 wound on a paper spool 24. The medical tape is usually formed in long rolls slit into individual rolls of tape.

Adhesive bandages come in a variety of configurations depending upon the application to which it will be placed.

The backing can be a woven or nonwoven fabric, such as vinyl, cloth or elastic materials and the like.

The backing for the bandage or medical tape may be clear, transparent, opaque. Normally it has a skin color. It may be solid, porous, permeable or perforated.

The gauze occupies a zone smaller than the size of the backing to permit exposed adhesive to secure the gauze to the wound. The gauze is typically cotton and may be coated to resist bonding to the wound.

All elements of the construction are sterilizable to prevent infection of a body part to which it is applied. Sterilization may be achieved by exposure to a sterilizing gas such as ethylene oxide or by radiation using actinic or electron beam radiation. Means and conditions for sterilization are disclosed in "Biocompatible Polymers, Metals and Composites" published by Technomic Publishing and edited by M. Szycher Ph.D incorporated herein by reference. Chapter 43 deals with sterilization of medical devices based on polymer selection and sterilization techniques and describe both ethylene oxide and radiation sterilization methods.

The emulsion based pressure-sensitive adhesives used in the adhesive bandage and tape constructions of the instant invention contain, on a percent by weight basis from 35 to about 60 percent by weight total, one or more alkyl acrylates containing about 4 to about 8 carbon atoms in the alkyl groups, and preferably total alkyl acrylate concentration, including mixtures of alkyl acrylates, preferably present in a total amount of from about 40 to about 50 percent by weight of the monomers. Useful alkyl acrylates include n-butyl acrylate, 2-ethylhexyl acrylate, isooctyl acrylate, and the like, with 2-ethyl hexyl acrylate being presently preferred.

The second monomeric component is one or more vinyl esters present in a total amount of from about 15 to about 35 percent by weight, preferably from about 20 to about 25 percent by weight based on total weight of the monomers, said vinyl esters containing from 2 to about 16 carbon atoms in the alkyl group of the acid. Representative of the vinyl esters include vinyl acetate, vinyl butyrate, vinyl propionate, vinyl isobutyrate, vinyl valerate, vinyl versitate, and the like. Vinyl acetate is preferred.

The third component of the emulsion polymers are one or more diesters of a dicarboxylic acid and mixtures thereof, present in a total amount of from about 20 to about 35 percent by weight based on the total weight of the monomers. Each ester group of the diester of the dicarboxylic acid independently contains from about 8 to about 16, preferably from about 8 to about 12, carbon atoms. The preferred diesters are di-2-ethylhexyl maleate (dioctyl maleate), di-2-ethylhexyl fumarate and mixtures thereof.

A fourth component of the emulsion polymers is at least one unsaturated carboxylic acid containing from about 3 to about 5 carbon atoms and present in a total amount of up to about 5 percent by weight of the polymer, preferably from to about 3 percent by weight. The unsaturated carboxylic acid includes, among others, acrylic acid, methacrylic acid, itaconic acid, and the like. Acrylic acid, methacrylic acid, and more preferably mixtures thereof, are presently preferred.

The emulsion adhesives are prepared in the presence of a reactive surfactant which polymerizes during formation of the polymer and becomes an integral part of the polymer. Preferred reactive surfactants include anionic vinyl functional monomers such as sodium vinyl sulfonate and sodium styrene sulfonate and the like. The reactive surfactant is present as part of the total surfactant system and in a positive amount up to about 0.4 percent by weight of the total monomers, preferably about 0.1 to about 0.25 percent by weight.

Presently preferred emulsion polymers contain exclusive of reactive monomers, about 48 percent by weight 2-ethylhexyl acrylate, about 21 percent by weight vinyl acetate, about 29 percent by weight di-2-ethylhexyl maleate, about 1 percent by weight acrylic acid, and about 1 percent by weight methacrylic acid.

The monomer proportions are adjusted in such a way that the adhesive has a glass transition temperature less than about $-20°$ C., preferably less than about $-30°$ C., giving a good balance of adhesion and tack at room temperature and low temperature. The emulsion polymers have a very broad glass transition temperature range of from $15°$ to $30°$ C., e.g. $-22°$ to $-52°$ C., which is unusual among acrylic polymers conventional acrylic polymers, for instance, have a glass transition temperature range of only 10 to $15°$ C. Depending on polymerization conditions, copolymers showing two distinct glass transition temperatures, one in the region of $-45°$ to $-60°$ C. and the other in the region of $15°$ to $-30°$ C., have been observed.

Gel content or percent insolubles in the emulsion polymers, as formed, is in the range of 50 to 70 percent by weight which provides excellent cohesive strength without the use of multifunctional monomers. In this regard, gel represents the amount of polymer which is insoluble in tetrahydrofuran expressed in percent by weight and determined by the membrane gel partitioning method. In this method, about 600 to 800 milligrams of 100 percent solid polymer is weighed onto a millipore membrane disk of 5 micrometer porosity. The disk is heat sealed and transferred to a scintillation vial. About 20 milliliters of tetrahydrofuran is added to the vial and the vial is rotated on a shaker for 16 to 24 hours. The sealed disk is then removed, washed with tetrahydrofuran, and dried first by placing it on a Whatman No. 1 filter paper, followed by exposure to $100°$ C. in the oven for a few hours. The dried disk is weighed and the insoluble portion of the polymer determined by the equation:

$$\text{percent insoluble} = \frac{(b-c) \times 100}{a} = \% \text{ gel}$$

wherein
- a = total weight of 100 percent solids polymer
- b = the weight of the polymer plus membrane before tetrahydrofuran treatment
- c = polymer plus membrane remaining after tetrahydrofuran treatment.

Polymer properties can be further modified to fit end use applications by inclusion of multifunctional monomers and the use of other chemical cross-linking agents. Other aids which may be used to develop cross-linking include thermal cross-linking and cross-linking by actinic and electron beam radiation. Cross-linking may occur to some degree during sterilization by radiation but without having an adverse effect on adhesive performance.

The emulsion polymers are prepared by polymerization under conditions of agitation in an autogenous atmosphere in the presence of suitable polymerization initiators such 15 as peroxydisulfate and peroxides. Depending on desired polymer properties including gel content the preferred levels of these initiators are in the range of from about 0.5 to about 1.0 percent by weight based on the total weight of the monomers. The presently preferred initiators are potassium persulfate, t-butyl hydrogen peroxide, and the like. Level of agitation will vary depending on the system and will influence conversion. Typically, about 30 to 50 percent of the total initiator is added along with an initial monomer charge to the reactor, and the rest is added along with the balance monomers during polymerization over a period of from about 4 to about 5 hours. For the polymer to be free from coagulum and to maintain grit levels less than 20 ppm, it is desirable to maintain the pH of the emulsion during polymerization between from about 2 to about 4, preferably from about 2.5 to about 4. This can be achieved by the use of buffers such as sodium bicarbonate and sodium acetate, typically in amounts up to 0.3 percent by weight based on the weight of the monomer.

The stabilizer system used during polymerization contains a combination of anionic and nonionic surfactants present in an amount up to about 3.5 percent by weight based on the weight of the monomers. A suitable anionic surfactant is the sodium salt of an ethoxylated nonylphenol sulfate, and a suitable nonionic surfactant is ethoxylated nonylphenol. The best balance of properties is achieved by maintaining the anionic to nonionic surfactant ratio approximately 3 to 1.

The emulsion polymers are produced at high solids level content, typically about 50 to about 70 percent by weight reaction is carried out at temperatures from 70° to 85° C. with an initial charge of up to about 10 percent by weight of the total monomers, with the balance of the monomers being added to the emulsion reaction system over a period of about 4 to about 5 hours, with total monomer conversion approaching 100 percent.

It is possible to modify the rheology of the polymer for coating purposes by use of conventional thickeners such as SCT-270 manufactured and sold by Union Carbide and present in an amount up to 0.2 percent by weight. Although not required, it is also feasible to modify the properties by the use of tackifiers and the like.

Chain transfer agents such as n-dodecyl mercaptan (n-DDM) and higher levels of initiator may be used to lower polymer molecular weight. An optimum level of n-DDM in this invention is up to about 0.025 percent by weight of the monomers, preferably about 0.005 to about 0.01 percent by weight, and to employ a level of initiator of about 0.5 to about 0.75 percent by weight based on the weight of the monomer composition. Amounts exceeding these levels can result in cohesive failure in peel adhesion.

EXAMPLE

To one liter reactor equipped with a reflux condenser, a thermocouple, a pitched turbine agitator and a nitrogen inlet tube, there was charged a solution containing 75 g of deionized water, 4 g of sodium vinyl sulfonate (25 percent w/w solution in water) and 0.36 g of an anionic surfactant (Alipal CO-433, a sodium salt of ethoxylated nonylphenol sulfate manufactured and sold by GAF Chemical Co.). 500 grams of monomer mix consisting of 43% by weight 2-ethylhexyl acrylate, 29% by weight di-2-ethylhexyl maleate, 21% by weight vinyl acetate, 17% by weight acrylic acid and 17% by weight methacrylic acid was added to 115 g of water containing 44.63 g of Alipal CO-433 and 6.44 g of Igepal CO-887, an ethoxylated nonylphenol nonionic surfactant manufactured and sold by GAF Chemical Co., and agitated to make a pre-emulsion. The reactor charge was heated under nitrogen to 70° C., to which was added 24.25 g of a potassium persulfate solution (3.78 percent w/w solution in deionized water). Sixty-six grams of the pre-emulsified monomer and 12.125 g of potassium persulfate solution were added to the reactor over 20 to 30 minutes. After the temperature reached a steady state, the remaining monomer pre-emulsion and a 1.8 percent aqueous solution of potassium persulfate buffered with sodium bicarbonate were introduced into the reactor at respective rates of 2.5 and 0.32 g/min. for a period of about 240 minutes. The reactor temperature was maintained between 70° to 82° C. After the end of feed, the reactor temperature was raised to 83° to 85° C. and maintained for 90 minutes. Once the polymerization was complete, the contents were cooled to ambient temperature and discharged. The polymer had 59.27 percent solids and a final pH of 3.8.

The emulsion adhesive was laboratory coated onto a vinyl backing at a coat weight of 35 g/m² and subjected to electron beam (EB) radiation to determine the effect on adhesive properties. The results are shown in Table 1.

TABLE 1

|  | EB Dosage in Megarods | | |
|---|---|---|---|
|  | 0 | 2.5 | 5.0 |
| Adhesion to stainless steel (SS), (lbs/in) | 1.9 | 2.1 | 1.7 |
| Looptack to SS, (lbs/in) | 3.0 | 3.0 | 2.7 |
| Static shear, (min, 1" × 1", 500 g) | 20 | 30 | 53 |

The emulsion adhesive was also pilot coated onto vinyl having release surfaces as used for tape manufacture. The effect of electron beam radiation on properties as shown in Table 2.

TABLE 2

|  | EB Dosage in Megarads | |
|---|---|---|
|  | 0 | 2.5 |
| Adhesion to SS, (lbs/in) | 1.5 | 1.5 |
| Adhesion to | 1.5 | 1.6 |

TABLE 2-continued

| | EB Dosage in Megarads | |
|---|---|---|
| | 0 | 2.5 |
| glass, (lbs/in) Adhesion to vinyl, (lbs/in) | 1.80 | 1.92 |
| Looptack to SS, (lbs/in) | 1.80 | 1.88 |
| Static Shear (min) (¾" × 1", 250 g) | 2774 | 5000 |

The results make clear that over the dosage levels tested there was minimal reduction in adhesion at the higher dosage level of 5.0 megarads and no effect at 2.5 megarads. There was, however, a significant increase in shear indicating internal cross-linking had occurred. This improves cohesive strength.

In another screening test the unradiated laminate when applied to skin withstood the action of several days of hot showers without separating from the skin.

What is claimed is:

1. A combination for use as a medical tape or bandage construction, said combination comprising:
   (a) a sterilizable backing;
   (b) a sterilizable inherently tacky, pressure-sensitive adhesive polymer applied to one side of said backing, said adhesive formed by emulsion polymerization and comprising on a polymerized basis and based on the total weight of the monomers:
      (i) at least one alkyl acrylate containing from about 4 to about 8 carbon atoms in the alkyl group, the total amount of alkyl acrylate present being from about 35 to about 60 percent by weight;
      (ii) at least one vinyl ester containing from 2 to about 16 carbon atoms in the alkyl group of the acid, the total amount of the vinyl ester present being from 15 to about 35 percent by weight;
      (iii) at least one diester of a dicarboxylic acid in which each alkyl group of the diester independently contains from about 6 to about 12 carbon atoms, the total of the diesters present being in amount from about 20 to about 40 percent by weight; and
      (iv) at least one unsaturated carboxylic acid containing from about 3 to about 5 carbon atoms, present in the total of the unsaturated carboxylic acid in an amount up to about 5 percent by weight, said polymer being formed in the presence of a reactive surfactant which is a vinyl functional monomer, and having a gel content of from about 50 to 70 percent by weight of the polymer prior to sterilization.

2. The combination as claimed in claim 1 in which the alkyl acrylate is present in a total amount of from about 40 to about 50 percent by weight of the monomers.

3. The combination as claimed in claim 1 in which the alkyl acrylate comprises 2-ethylhexyl acrylate.

4. The combination as claimed in claim 1 in which the Vinyl ester is present in a total amount of from about 20 to about 25 percent by weight based on the total weight of the monomers.

5. The combination as claimed in claim 4 in which the vinyl ester is vinyl acetate.

6. The combination as claimed in claim 1 in which the diester of a dicarboxylic acid independently contains from about 8 to about 12 carbon atoms in each alkyl group.

7. The combination as claimed in claim 6 in which the diester of the dicarboxylic acid is selected from the group consisting of di-2-ethylhexyl maleate, di-2-ethylhexyl fumarate, and mixtures thereof.

8. The combination as claimed in claim 1 in which the unsaturated carboxylic acid is present in an amount of from about 1 to about 3 percent by weight of the total monomers.

9. The combination as claimed in claim 8 in which the unsaturated carboxylic acid is selected from the group consisting of acrylic acid, methacrylic acid, and mixtures thereof.

10. The combination as claimed in claim 1 in which the vinyl functional monomer is selected from the group consisting of sodium vinyl sulfonate and sodium styrene sulfonate and present in an amount up to 0.4 percent by weight based on the total weight of the monomers.

11. The combination as claimed in claim 10 in which the reactive surfactant is present in an amount of 0.1 to about 0.25 percent by weight of the total monomers.

12. The combination as claimed in claim 1 in which the alkyl acrylate is selected from the group consisting of isooctyl acrylate, 2-ethylhexyl acrylate and mixtures thereof; the vinyl ester is vinyl acetate, the diester of dicarboxylic acid is selected from the group consisting of di-2-ethylhexyl maleate, di-2-ethylhexyl fumarate and mixtures thereof, the unsaturated carboxylic acid is selected from the group consisting of acrylic acid, methacrylic acid and mixtures thereof and the reactive surfactant is selected from the group consisting of sodium vinyl sulfonate, sodium styrene sulfonate and mixtures thereof.

13. The combination as claimed in claim 1 in which the pressure-sensitive adhesive polymer comprises from about 40 to about 50 percent by weight 2-ethylhexyl acrylate, from about 20 to about 25 percent by weight vinyl acetate, from about 20 to about 35 percent by weight of a diester of a dicarboxylic acid selected from the group consisting of di-2-ethylhexyl maleate, di-2-ethylhexyl fumarate and mixtures thereof, about 1 to about 3 percent by weight of an unsaturated carboxylic acid selected from the group consisting of acrylic acid, methacrylic acid and mixtures thereof, and an anionic reactive surfactant selected from the group consisting of sodium vinyl sulfonate and sodium styrene sulfonate present in a positive amount of up to about 0.4 percent by weight of the total monomers.

14. A pressure-sensitive adhesive polymer as claimed in claim 13 in which a reactive surfactant is present in an amount of from about 0.1 to about 0.25 percent by weight.

15. The combination as claimed in claim 1 in which the emulsion pressure-sensitive adhesive polymer contains on a polymerized basis, about 48 percent by weight 2-ethylhexyl acrylate, about 21 percent by weight vinyl acetate, about 29 percent by weight di-2-ethylhexyl maleate, about 1 percent by weight acrylic acid, and about 1 percent methacrylic acid.

16. The combination as claimed in claim 1 further including a gauze adhered to a portion of the pressure-sensitive adhesive layer.

17. The combination as claimed in claim 16 in which a release liner is at least in contact with that portion of the pressure-sensitive adhesive not in contact with the gauze.

18. The combination as claimed in claim 13 further including a gauze adhered to a portion of the pressure-sensitive adhesive layer.

19. The combination as claimed in claim 18 in which a release liner is at least in contact with that portion of the pressure-sensitive adhesive not in contact with the gauze.

20. A bandage construction comprising:
   (a) a sterilized backing;
   (b) a sterilized inherently tacky, pressure-sensitive adhesive layer on one side of said backing, said adhesive formed by emulsion polymerization and comprising on a polymerized basis and based on the total weight of the monomers:
      (i) about 48 percent by weight of an alkyl acrylate selected from the group consisting of 2-ethyl hexylacrylate and isooctyl acrylate;
      (ii) about 29 percent by weight of a diester of a dicarboxylic acid selected from the group consisting of di-2-ethylhexyl maleate and di-2-ethylhexyl fumarate and;
      (iv) about 1 percent by weight acrylic acid;
      (v) about 1 percent by weight methacrylic acid, said polymer being formed in the presence of a reactive surfactant and a gel content of at least 50 percent by weight.
   (c) a gauze adhered to a portion of the pressure-sensitive adhesive layer;
   (d) a release liner extending over said adhesive liner and gauze.

* * * * *

UNITED STATES PATENT AND TRADEMARK OFFICE
CERTIFICATE OF CORRECTION

PATENT NO. : 5,183,459
DATED : February 2, 1993
INVENTOR(S) : Margaret M. Bernard It is certified that error appears in the above-indentified patent and that said Letters Patent is hereby corrected as shown below:

Column 1, line 22, before "currently" insert -- are --.
Column 1, line 25, change "Self adhesive" to -- Self-adhesive --.
Column 1, line 33, change "hypoalergenic" to -- hypoallergenic --.
Column 1, line 47, change "hypoalergenic" to -- hypoallergenic --.
Column 1, line 47, change "current" to -- currently --.
Column 1, line 61, change "hypoalergenic" to -- hypoallergenic --.

Column 2, line 12, after "about" insert -- 1 --.
Column 2, line 59, change "tapes" to -- tape --.

Column 3, line 8, before "FIGS." insert -- In --.
Column 3, line 10, after "FIG." insert -- 1 --.
Column 3, line 12, change "self adhesive" to -- self-adhesive --.

Column 4, line 11, after "from" insert -- 1 --.
Column 4, line 39, after "polymers" insert a period.
Column 4, line 39, change "conventional" to -- Conventional --.
Column 4, line 44, change "15°" to -- -15° --.

Column 5, line 19, after "such" delete "15".
Column 5, line 51, after "weight" insert a period.
Column 5, line 51, change "reaction" to -- Reaction --.

UNITED STATES PATENT AND TRADEMARK OFFICE
CERTIFICATE OF CORRECTION

PATENT NO. : 5,183,459
DATED : February 2, 1993
INVENTOR(S) : Margaret M. Bernard It is certified that error appears in the above-identified patent and that said Letters Patent is hereby corrected as shown below:

Column 6, line 48, in TABLE 1, change "Megarods" to -- Megarads --.
Column 6, line 61, change "effect" to -- effects --.
Column 6, line 62, before "shown" change "as" to -- are --.

In the Claims

Column 7, line 43, before "amount" insert -- an --.

Column 10, line 12, after "weight" change the period to a semicolon.

Signed and Sealed this

Nineteenth Day of April, 1994

Attest:

BRUCE LEHMAN

Attesting Officer

Commissioner of Patents and Trademarks